US00PP14545P29

(12) United States Plant Patent
Corr

(10) Patent No.: US PP14,545 P2
(45) Date of Patent: Feb. 17, 2004

(54) DIASCIA PLANT NAMED 'BALWHISLAPI'

(50) Latin Name: *Diascia barberae*
Varietal Denomination: Balwhislapi

(75) Inventor: Brian Corr, Sycamore, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/329,823

(22) Filed: Dec. 26, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Wood, Phillips, Katz, Clark & Mortimer

(57) ABSTRACT

A new and distinct Diascia plant named 'Balwhislapi', characterized by its lavender colored flowers, spreading and trailing growth habit, and medium green foliage.

2 Drawing Sheets

Latin name of genus and species of plant claimed: *Diascia barberae.*
Variety denomination: 'Balwhislapi'.

BACKGROUND OF INVENTION

The present invention comprises a new and distinct Diascia plant, botanically known as *Diascia barberae*, and hereinafter referred to by the cultivar name 'Balwhislapi'.

The new cultivar was developed by the inventor in a controlled breeding program during February 1999, at Elburn, Ill. The objective of the breeding program was the development of Diascia cultivars with a well-branched, spreading growth habit, continuous flowering and medium green foliage.

The female (seed) parent of 'Balwhislapi' was the Diascia variety 'Langhorne Lavender' (protection status unknown by inventor), characterized by its lavender colored flowers. The male (pollen) parent of 'Balwhislapi' was the Diascia variety 'Red Start' (protection status unknown by inventor), characterized by its red colored flowers, small leaves of a medium green color and upright, spreading growth habit. 'Balwhislapi' was discovered and selected in June 1999 as a single flowering plant from within the progeny of the above stated cross and was designated 10700-3.

Asexual reproduction of the new cultivar at West Chicago, Ill. was carried out by the use of terminal stem cuttings and has demonstrated that the characteristics of the new cultivar as herein described are firmly fixed and retained through successive generations of such asexual propagation.

SUMMARY OF INVENTION

It was found that the cultivar of the present invention:

(a) exhibits lavender colored flowers, (b) forms foliage of a medium green color, and (c) exhibits a spreading and trailing growth habit.

The new cultivar can be compared to the commercially available Diascia variety, 'Strawberry Sundae' (U.S. Plant Pat. No. 11,488). In side-by-side comparison, plants of the new cultivar are wider, have leaves of a lighter green color, are more floriferous and have smaller flowers than those of 'Strawberry Sundae'.

BRIEF DESCRIPTION OF PHOTOGRAPH

The accompanying photographs show as nearly true as it is reasonably possible to make the same in color illustrations of this type, typical flower and foliage characteristics of the new cultivar. The plants were grown for 11 weeks in a greenhouse at West Chicago, Ill.

DETAILED BOTANICAL DESCRIPTION

Figure 1:
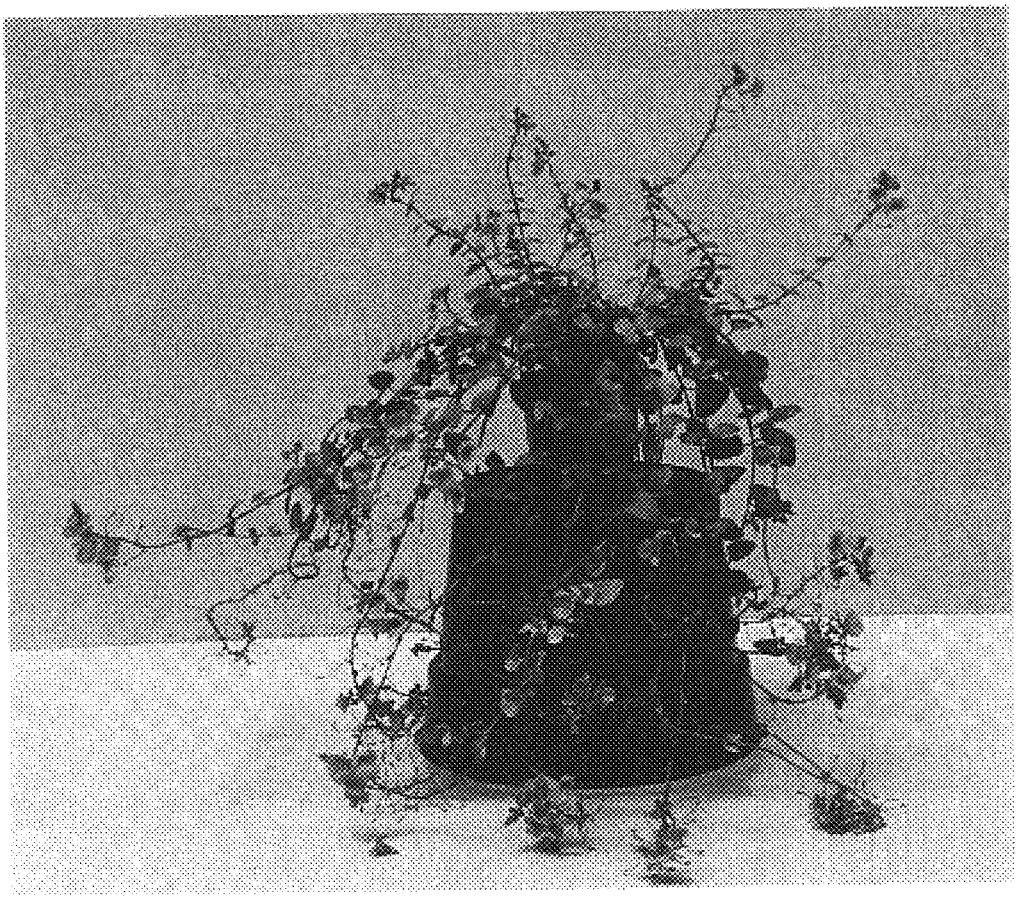
FIG. 1 illustrates the overall growth habit of the new cultivar.
Figure 2:
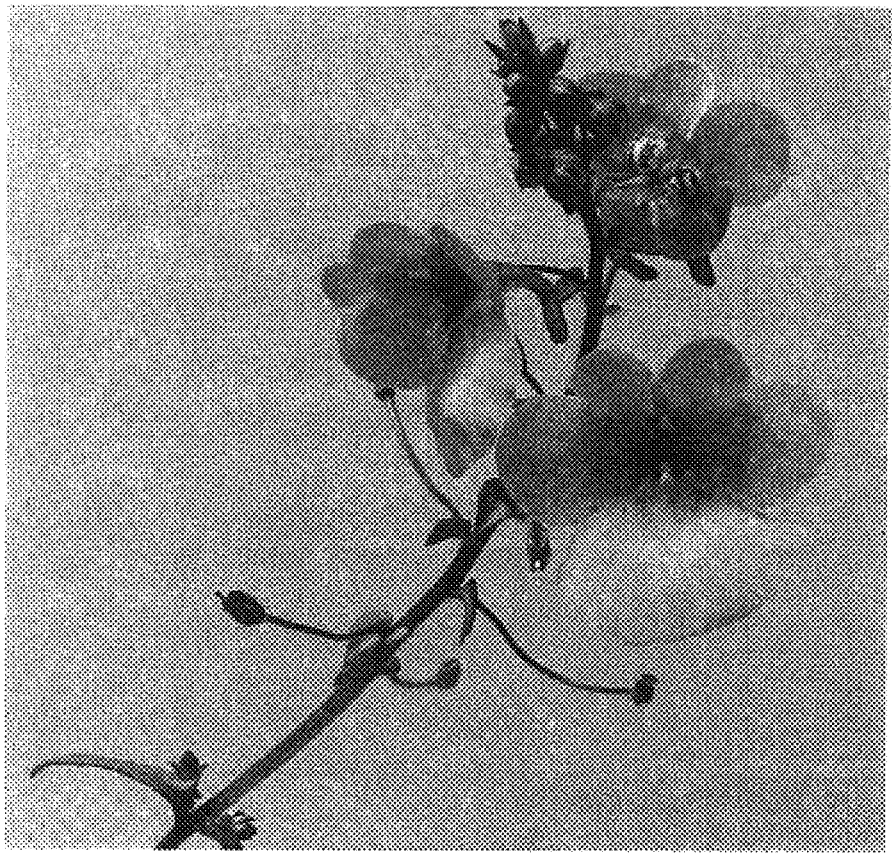
FIG. 2 illustrates a close up view of individual flowers of the new cultivar.

The new cultivar has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Apr. 24, 2002. The readings were taken between 1:00 and 3:00 p.m. under natural daylight conditions. The plants were produced from cuttings taken from stock plants and were grown in a double polycarbonate covered greenhouse under conditions comparable to those used in commercial practice. The plants were grown for 10 weeks while utilizing a soilless growth medium and maintaining temperatures of approximately 62° to 75° F. (17° to 24° C.) during the day and approximately 52° to 60° F. (11° to 15° C.) during the night and light levels of 5,000 to 8,000 footcandles.

Classification:
*Botanical.*—*Diascia barberae* cultivar 'Balwhislapi'.
Parentage:
*Female parent.*—Diascia variety 'Langhorne Lavender'.
*Male parent.*—Diascia variety 'Red Start'.

Propagation:

*Type cutting.*—Terminal tip.

*Time to initiate roots.*—Approximately 14 to 21 days.

*Root description.*—Fibrous, branching.

Plant description:

*Crop time.*—Approximately 5 to 7 weeks from planting of rooted cuttings in a 10 cm pot.

*Habit of growth.*—Vigorous. Pinching improves branching. A mature plant, 10 weeks after the planting of a rooted cutting, measures approximately 24 cm in height and approximately 65 cm in width with approximately 3 main branches and 16 lateral flowering branches.

*Form.*—Spreading, trailing.

*Lateral branch.*—Shape: Square. Length: Approximately 25.6 cm. Diameter: Approximately 1.3 mm. Texture: Sparsely covered with glandular pubescence. Internode length at middle of branch: Approximately 2.5 cm. Color: 146C with overlay of 187B.

*Foliage.*—Type: Simple. Arrangement: Opposite. Shape: Ovate. Margin: Serrate. Apex: Acute. Base: Cordate. Texture: Very sparsely pubescent. Quantity per lateral branch: Approximately 18. Leaf length: Approximately 2.5 cm. Leaf width: Approximately 1.7 cm. Leaf orientation to stem: Acute. Leaf fragrance: None. Upper surface of mature foliage is 137A and lower surface is 148B. Upper and lower surfaces have pinnate venation of 144C. Petiole length: Approximately 6 mm. Petiole diameter: Approximately 1 mm. Petiole color: Upper surface is 143C, lower surface is 143D. Upper and lower surfaces of petiole are slightly pubescent.

Flowering description:

*Flowering habit.*—Freely flowering.

*Natural flowering season.*—Year round in greenhouse environment and spring through autumn in outdoor garden.

*Flower arrangement.*—Terminal racemes.

Flower description:

*Type.*—Solitary, five lobed and zygomorphic.

*Fragranc.*—None.

*Aspect.*—Concave.

*Corolla.*—Width: Approximately 1.7 cm. Length: Approximately 1.7 cm. Depth: Approximately 9 mm.

*Petals.*—Number: Five, fused at base. Aspect: Cupped. Two upper petals: Length is approximately 4 mm, width is approximately 5 mm. Lateral petals: Length is approximately 6 mm, width is approximately 7 mm. Sharply curved nectar spurs form at base of each of the lateral petals. Nectar spur length: Approximately 7 mm. Nectar spur color: 70A with 77A at tip. Lower petal: Length is approximately 1 cm, width is approximately 1.4 cm. All petals: Margin: Entire. Apex: Obtuse. Surface: Glabrous and iridescent. Color: Upper surface of upper petal is between 75A and 75B at margin, 70B around indentation at base, with venation of 72C. Color of indentation at base is 1A. Lower surface of upper petal is 75B at margin, 75A at base. Upper surface of lateral petals is between 75A and 75B. Lower surface of lateral petals is 75B at margin and 74A at base. Upper surface of lower petal is between 75A and 75B. Lower surface of lower petal is 75B at margin and 75D at base.

*Sepals.*—Quantity: 5. Shape: Lanceolate. Length: Approximately 3 mm. Width: Approximately 1 mm. Apex: Acute. Margin: Entire. Calyx shape: Star. Calyx length: Approximately 3 mm. Calyx diameter: Approximately 6 mm. Calyx texture: Densely glandular-pubescent with glands of 93A on outer surface. Inner surface is glabrous. Color of inner and outer surface is 144C.

*Pedicels.*—Length: Approximately 1.4 cm. Diameter: Less than 1 mm. Texture: Densely glandular-pubescent. Color: 144C with glands of 93A.

*Peduncle.*—Length: Approximately 6 cm. Diameter: Approximately 1 mm. Aspect: At acute angle to branch. Texture: Moderately pubescent. Color: 187D.

*Bud.*—Shape: Triangular. Length: Approximately 5.2 mm in length. Diameter: Approximately 5.9 mm. Color: 72D.

*Reproductive organs.*—Androecium: There are 4 stamens. Filament length:

Approximately 2 mm. Filament color: 83B. filament texture: Glandular. Anther shape: Cup. Anther length: Is less than 1 mm. Anther color: 3B. Pollen is abundant and 3B in color. Gynoecium: There is one pistil, 5 mm in length. Stigma shape: Round. Stigma length: Less than 1 mm. Stigma color: 151D. The style length is approximately 2 mm and the color is 150C. Ovary length is approximately 2 mm and color is N144D.

Seed production: Seed production has not been observed.

Disease resistance: Resistance to pathogens has not been observed.

Hardiness zone: 'Balwhislapi' is hardy in zones nine (9) and above.

I claim:

1. A new and distinct *Diascia barberae* plant named 'Balwhislapi' substantially as herein shown and described, which:

(a) exhibits lavender colored flowers, (b) forms medium green foliage, and (c) exhibits a spreading and trailing growth habit.

* * * * *